United States Patent
Mattes et al.

(10) Patent No.: US 6,974,792 B2
(45) Date of Patent: Dec. 13, 2005

(54) ALPHA 1-ANTITRYPSIN PREPARATION AS WELL AS A METHOD FOR PRODUCING THE SAME

(75) Inventors: Erwin Mattes, Perchtoldsdorf (AT); H. Peter Matthiessen, Vienna (AT)

(73) Assignee: Baxter Aktiengesellschaft, Vienna (AU)

( * ) Notice: Subject to any disclaimer, the term of this patent is extended or adjusted under 35 U.S.C. 154(b) by 454 days.

(21) Appl. No.: 09/963,341

(22) Filed: Sep. 24, 2001

(65) Prior Publication Data

US 2002/0082214 A1    Jun. 27, 2002

Related U.S. Application Data

(63) Continuation of application No. 09/445,590, filed as application No. PCT/AT98/00130 on May 20, 1998.

(30) Foreign Application Priority Data

Jun. 10, 1997  (AT) .................................... 1007/97

(51) Int. Cl.$^7$ .......................... A61K 38/00; C12N 9/50; C12N 7/04
(52) U.S. Cl. ........................... 514/2; 435/219; 435/236
(58) Field of Search .............................. 435/219, 226; 514/2

(56) References Cited

U.S. PATENT DOCUMENTS 5,610,285 A * 3/1997 Lebing et al. ............... 530/416
5,760,179 A * 6/1998 Fitchmun ..................... 530/350

OTHER PUBLICATIONS

Product Information for CHT Cermain Hydroxyapatitle and Bio-gel Hydroxyapatite from the website: http://bio-rad-.com/B2B/BioRad/product/br_categoy.*
Chan et al. "Purification and Chemical Composition of Human alpha 1-Antitrypsin of the MM Type" FEBS Lett. (1973) 35(1): 79-82.*

* cited by examiner

Primary Examiner—Jean C. Witz
Assistant Examiner—Susan Hanley
(74) Attorney, Agent, or Firm—Patrick S. Eagleman

(57) ABSTRACT

A native, chromatographically purified α1-AT preparation having a purity of at least 0.7 PU/mg protein and a relative plasma α1-AT activity of at least 120% is disclosed. The ratio of active to inactive α1-AT is higher than in plasma.

Furthermore, a method of producing this preparation is disclosed, as well as the use of a carrier material, e.g. an inorganic carrier material such as hydroxylapatite for separating active α1-AT from inactive α1-AT.

15 Claims, No Drawings

ALPHA 1-ANTITRYPSIN PREPARATION AS WELL AS A METHOD FOR PRODUCING THE SAME

This application is a continuation of application Ser. No. 09/445,590, filed on Mar. 13, 2000, which is a 35 USC 371 application of PCT/AT98/00130, filed on May 20, 1998, which claims the priority of Austrian patent application A1007/97, filed Jun. 10, 1997.

The invention relates to alpha 1-antitrypsin preparations, methods of producing the same as well as uses for these preparations.

Alpha 1-antitrypsin ($\alpha$1-AT) is a protein occurring in plasma which, on account of its structural and functional properties, is classified in the super family of serpins (serine protease inhibitors). On the basis of its serine-protease inhibiting effect, $\alpha$1-AT is also known under the name of $\alpha$1 proteinase inhibitor. $\alpha$1-AT is responsible for approximately 90% of the tryptic inhibition capacity of normal plasma, and therefore it often is also termed major plasma serpin. Of particular physiological importance is the inhibitory activity of $\alpha$1-AT relative to elastase.

$\alpha$1-AT primarily is a protective protein, by which cells are to be protected from liberated proteolytic enzymes. It is synthesized in the liver and secreted into plasma, where it has a half life of approximately 6 days. The normal concentration of $\alpha$1-AT in plasma is 1.3 g/l.

$\alpha$1-AT is a relatively small and polar molecule which rapidly gets into the cell liquids and can become effective there. Human $\alpha$1-AT consists of one single polypeptide chain having 394 amino acid residues with three glycosylation positions at the asparagine residues of positions 46, 83 and 247. While at asparagine 46 and 247, there are both two and three-antennal sialysated carbohydrate side chains, on asparagine 83 merely one sialysated bi-antennal side chain is present (Carrell et al., Nature 298 (1982), 329–334).

The protein chain of $\alpha$1-AT exists in plasma in two forms, wherein in one form an N-terminal pentapeptide is removed.

These carbohydrate side chains, but also the possible pentapeptide removal result in quite a pronounced microheterogeneity which may also change in one and the same individual. Thus it is found that substantial changes in the proportions of these iso-forms of the $\alpha$1-AT molecules occur in the course of inflammations or during an administration of estrogen which probably is due to the fact that as a consequence of the stress situation, the partially desialysated forms are degraded more rapidly so as to reach normal plasma levels again more rapidly (Patterson, Comp. Biochem. Physiol. 100 B (3) (1991), 439–454).

The eerine protease inhibiting action of $\alpha$1-AT is a consequence of the formation of Estable 1:1 complexes between $\alpha$1-AT and the target proteane, $\alpha$1-AT thus acts as a kind of "suicide substrate" by which the further protease reaction of the serine protease is blocked. The action of $\alpha$1-AT primarily is inhibited by liberated radicals which likewise are formed in the course of inflammations. Physiologically, this oxidation lability probably serves to block the enzyme-inhibiting activity of $\alpha$1-AT in the immediate vicinity of the inflammation, so that proteases, such as elastase and kathepsin G, may become fully effective in fighting e.g. bacteria that trigger an inflammation.

The oxidation lability of $\alpha$1-AT is, however, primarily detrimental where $\alpha$1-AT or the liquid containing $\alpha$1-AT, respectively, is exposed, such as e.g. in the liquids of the respiratory tract. Thus, the elastic tissue of the lungs is protected from surface attacks substantially by two inhibitors, the human secretory leucocyte protease inhibitor which is mainly found in the upper respiratory tract, and $\alpha$1-AT which is primarily found in the lower respiratory tract. Although normally more than enough inhibitory capacity is available for defending the lower respiratory tract, an excessive exposition to free radicals, e.g. when smoking heavily, may give rise to problems (in heavy smokers, the inhibitory capacity of $\alpha$1-AT is approximately cut in half).

In the meantime, more than 70 qualitative and quantitative variants of human $\alpha$1-AT have become known which are inherited as autosomal co-dominant alleles. It being assumed that approximately 10% (!) of the European population are carriers of a pathologic variant of $\alpha$1-AT. Moreover, $\alpha$1-AT deficiencies are known and relatively wide spread. The most remarkable pathologic findings in connection with the $\alpha$1-AT gene variance are a degenerative lung disease starting at a relatively early age as well as a severe liver disease. Besides, also renal disorders, arthritis and malignant diseases are suspected of being connected with an $\alpha$1-AT gene variance. Primarily in case of lung disease, the latter is a direct consequence of the respective plasma level of $\alpha$1-AT which, due to the accumulated proteolytic damage, also causes a loss of lung elasticity. Thus, a heavy smoker suffering from a homozygotic $\alpha$1-AT deficiency is jeopardized twice and has a high risk of developing a severe emphysema already at an age of less than 40 years. As compared to the non-smoking homozygotic individual, his life time is shortened by 20 years.

In plasma, $\alpha$1-AT occurs both in an active as well as an inactive form (cf., e.g., Pajdak W. et al, Folia Histochemica et Cytobiologica, vol. 24 (1986), pp. 169–172).

A number of production methods for $\alpha$1-AT are known which comprise the fractionated precipitation of plasma with polyethylene glycol 4000, but also the processing of various plasma frations (Cohn fraction IV-1-precipitate or Kistler and Nitschmann Supernatant A or A+1) (Feldman and Winkelman, Blood Separation and Plasma Fractionation (1991), Wiley-Liss, Inc., pp. 341–383).

In more elaborate purifications, the respective blood fractions have been purified by means of DEAE cellulose, e.g. (Basis et al. (Vopr. Med. Khim. 33 (1) (1987), 54–59)), treated with affinity chromatographic materials or with cation exchanger chromatographic materials (EP-0 698 615-A1).

Basis et al. describe a method for purifying $\alpha$1-AT by ammonium sulfate precipitation of plasma and subsequent DEAE cellulose chromatography and hydroxylapatite chromatography. This method has constantly been employed in the presence of mercaptoethanol which is to protect the protein against oxidation of S-containing groups. Following the hydroxylapatite chromatography, $\alpha$1-AT is recovered in two fractions, yet the two proteins, $\alpha$1-AT and albumin, are not completely separated.

In the course of preparatory work carried out for the present invention it has now been found that with all the conventional production methods, in particular also with the methods according to Basis et al. and according to EP-0 698 615-A1, it has not been possible to completely separate the inactive $\alpha$1-AT constitutively present in plasma with the active $\alpha$1-AT, or to make a preparation by obtaining active isomers, respectively.

Thus it is an object of the present invention to provide a method by which an $\alpha$1-AT preparation can be recovered in which the ratio of active $\alpha$1-AT to inactive $\alpha$1-AT is improved in favor of active $\alpha$1-AT, i.e. by means of which inactive $\alpha$1-AT can selectively be separated from active $\alpha$1-AT.

A further object of the present invention consists in providing an α1-AT preparation which is improved over conventional preparations.

Thus, the subject matter of the present invention is a preparation on the basis of native, chromatographically purified α1-AT which has a purity of at least 0.7 PU/mg protein and a relative plasma α1-AT activity of at least 120%.

The relative plasma α1-AT activity is defined as the ratio of active to inactive α1-AT, this ratio in plasma being assumed to be 100% of relative plasma α1-AT activity. For the preparations provided according to the invention, this relative plasma α1-AT activity preferably is more than 130%, more preferably more than 140%, in particular more than 150%. In particular instances, the relative plasma α1-AT activity is also more than 160%. Because of their purity, in the products according to the invention the protein contained is approximately equal to the α1-AT protein, and thus the relative plasma α1-AT activity can be calculated in a simple manner.

In blood or in serum, respectively, a certain portion of α1-AT is always present in inactive form, i.e. it has practically no elastase-inhibiting activity, yet it is still immunoreactive. The total amount of (active and inactive) α1-AT can be determined by any conventional method, e.g. antigen-quantitating immunological methods, such as ELISA.

The reasons for the presence of inactive α1-AT may be manifold, α1-AT may, for instance, be inactive because of a cleavage of the molecule or because of an impaired conformation.

Since, normally, up to 20% of inactive α1-AT may be present in blood or serum, respectively, and the former could not be separated by conventional methods, the preparation according to the invention constitutes a substantial progress over conventional α1-AT preparations in which the inactive portion so far has always been "entrained". As has been mentioned, the concentration of α1-AT in normal plasma is 1.3 g/l, resulting in a specific activity of 0.77 PU (plasma units, determined in the elastase inhibition assay, cf. Example 3)/mg.

The α1-AT preparation according to the invention preferably contains at least the isomer with a pI value of between 4.3 and 4.4.

For, surprisingly, it has been shown that just because of the presence of this isomer, the activity of the α1-AT is very high. Since the isomer with a pI value of between 4.3 and 4.4 on account of its acidic nature in the prior art methods for recovering α1-AT has always been separated from the α1-AT fraction together with albumin, none of the α1-AT preparations so far contains amounts of this isomer worthy of mention. In the course of the present invention, however, the relevance of exactly this isomer with regard to the activity yield has been realized, and therefore, according to the invention, the production method preferably only comprises steps which do not allow a separation of this isomer from the remaining α1-AT or allow it to an unsubstantial extent, only, so that also the major portion of this acidic isomer is present in the final preparation.

Thus, the isomer distribution of the preferred preparation corresponds to that of the native protein, in particular that protein which is obtainable from a plasma pool. In particular, the isomer distribution of the α1-AT preparation according to the invention corresponds to a quadruplet band pattern when made visible by isoelectric focussing (IEF).

The IEF is particularly carried out with the gel Ampholine PAG plate IEF™ (pH 4.0–6.5, or pH 4.0–5.0) obtainable from Pharmacia according to the instructions provided by Pharmacia by using IEF markers from Sigmia (IEF Mix 3.6–6.6).

The isomer with a pI value of between 4.3 and 4.4 corresponds to the most acidic band. However, with pure or highly purified α1-AT preparations, respectively, it is just this isomer that is lacking or is contained therein to a slight extent, below the detection limit.

The α1-AT preparation according to the invention in particular has a high purity, e.g. a purity of more than 0.8 PU/mg, preferably a purity of more than 0.9 PU/mg, most preferred of more than 1 PU/mg. It has even been shown that according to the invention purities of more than 1.1 PU/mg, in particular more than 1.2 PU/mg, are attainable.

The preparation according to the invention usually contains less than 10%, preferably less than 5%, in particular less than 2%, of inactive α1-AT.

According to the present invention it is also possible to provide an α1-AT preparation which is substantially free from inactive α1-AT.

In the preparation according to the invention, the ratio of active α1-AT to inactive α1-AT is increased, in particular it is higher than that in human normal plasma. Thus, it is possible according to the present invention to obtain a hyperactive α1-AT or an α1-AT that can be termed nascent.

By normal plasma, according to the present invention a plasma standardized as regards its content of active α1-AT is to be understood. Standardizing, i.e. the determination of active α1-AT, may be effected by methods common therefor; e g. by inhibiting the elastase or trypsin activity, respectively.

The preparation according to the invention has the substantial advantage over the preparations of the prior art that the present preparation which is particularly intended for a pharmaceutical administration, because of its low content of inactive α1-AT is much more defined in terms of its efficacy than the known preparations, which is an enormnous advantage particularly in case of a medical use thereof.

Preferably, a preservative α1-AT is provided, in which the use of oxidation stabilizers, such as β-mercaptoethanol, can be avoided. Within the scope of the present invention, "preservative" thus means that the α1-AT is sufficiently stable also without the presence of oxidation stabilizers, such as β-mercaptoethanol, which was particularly surprising in view of the known high oxidation lability of α1-AT.

The preparation according to the invention can be produced departing from blood, plasma, serum or fractions thereof, but also departing from cell cultures, in particular recombinant cell cultures, or cell culture supernatants.

Preferably, the monomer content of the preparation according to the invention is at least 95%, preferably at least 98%.

A preferred embodiment of the preparation according to the invention consists in that the preparation is not only improved in terms of its content of active α1-AT, but that it is also present in high purity, e.g. of at least 90% (mg/mg of protein).

A subject matter of the present invention is also a pharmaceutical preparation comprising the α1-AT preparation according to the invention, optionally with pharmaceutically acceptable auxiliary substances, such as buffers, stabilizers, adjuvants, antioxidants, salts or excipients.

Since the present preparation is to be used primarily in the pharmaceutical field, a preferred embodiment consists in that the preparation is treated for inactivating pathogens possibly present therein. Suitably, the preparation is provided in storage-stable form, preferably as a lyophilisate, or as a (deep-frozen) solution, in particular as a solution suitable for i.v. administration, as an aerosol or as a spray. The preparation may also be provided in association with lipoeomes or phospholipids, respectively, or with other micro- or nano-particulate forms as is advantageous with certain forms of application.

A subject matter of the present invention is also a method of producing the α1-AT preparation of the invention by purifying an α1-AT-containing fraction which preferably is obtainable from a human plasma pool by adsorption chromatography in a manner that α1-AT is adsorbed, optionally inactive α1-AT is separated, and active α1-AT is recovered in a fraction by elution.

According to the present invention, by adsorption chromatography such a chromatography is to be understood in which the α1-AT is adsorbed (bound) to the chromatographic material. Finally, the desired fraction can be recovered by elution.

For the adsorption chromatography, e.g. an inorganic chromatographic material, such as, e.g., hydroxylapatite, preferably ceramic hydroxylapatite, can be used. The adsorption chromatography may, however, also be carried out on an anion exchanger, preferably in the presence of a detergent.

As the anion exchanger, preferably materials based on carbohydrates or vinyl polymers are used which have proven suitable in laboratory work and industrial applications, in particular commercially available products, such as, e.g., DEAE-Sephacel®, DRAE-Sephadex®, DEAE-Sepharose® CL6B, DEAE-Sepharose® Fast Flow, QAS-Sephadex®, Q-Sepharose® Fast Flow, Q-Sepharose Big Beads®, Q-Sepharose® High Performance (Pharmacia); DEAE-Trisacryl, DEAE-Spherodex®, Q-Hyper-D® (Sepracor); DEAE-Toyopearl®, QAE-Toyopearl®, Toyopearl SuperQ® (Tosohaas); Fractogel®-EMDT, -TMAE or other Fractogel materials, Licrospher 1000 TMAE®, Licrospher 1000 DEAE® und Licrospher 4000 DMAE® (Merck); Macroprep DEAE®, Macroprep Q® (BioRad); Protein PAK DEAE® (Waters), the treatment with a strong anion exchanger, e.g. Q-Sepharose, being particularly preferred. The exact conditions under which the recovery of active α1-AT is effected may vary depending on the exchanger material used; however, they can be found and optimized for the respective material easily and without great efforts by the skilled artisan who has knowledge of the present invention.

At the adsorption chromatography or prior thereto, the starting material preferably is not incubated or incubated for a very short period of time only (e.g. a few minutes). Adsorption chromatography and recovery, respectively, of the α1-AT is particularly effected under such conditions that the isomer having a pI value of between 4.30 and 4.40, in particular between 4.34 and 4.39 is retained, and particularly preferably such that the spectrum of active isomers is retained also during and after the purification or treatment, respectively. These conditions can easily be optimized by the skilled artisan by trying various elution buffers for the respective adsorption materials used, since the isomer with a pI value of between 4.3 and 4.4 or the fraction in wich this isomer is contained, respectively, can easily be detected by means of IEF. In doing so, care must be taken that this acidic isomer is not separated together with albumin. This, however, is easily possible for the skilled artisan, e.g. by means of gel electrophoresis or by an IEF check of the eluted fractions (and the detection of acidic α1-AT and albumin), respectively.

In a further preferred embodiment, no chromatography is carried out on a cation exchanger, in particular not a cation exchanger chromatography at low pH.

By detergent (tenside), usually a surface-active organic substance is to be understood, in particular products of organic synthesis. According to the invention, preferably non-ionic detergents are used, such as polyether, in particular alkyl-phenol-polyglycol ether, products of ethoxylation of fatty acids, fatty acid amides, fatty aminee, fatty alcohols, aminoxides, fatty acid esters of polyalcohols and sugar esters. The detergent (tenside) particularly does not have a denaturing action on proteins. For the purposes of the present invention, a tenside of the group of polysorbates (e.g. Tween) and a tenside from the Triton® group are particularly preferred.

In the method according to the invention, according to a preferred embodiment, the adsorption chromatography may be preceded or followed by a further treatment, such as, e.g., precipitation, filtration, gel filtration, a treatment with an inorganic carrier material or a chromatographic purification. Hydroxylapatite has proven to be a preferred inorganic carrier material, ceramic hydroxylapatite being particularly preferred. In a further preferred embodiment, the adsorption chromatography on an anion exchanger, preferably in the presence of a detergent, is combined with an adsorption on hydroxylapatite.

In the course of work carried out in connection with the present invention, surprisingly it has been shown that it is possible under certain circumstances to effect also a separation of active α1-AT from inactive α1-AT by a treatment with inorganic materials, such as hydroxylapatite. Such effect particularly occurs if the α1-AT has already been substantially separated from albumin.

Therefore, also the treatment of a pre-purified α1-AT preparation with an inorganic carrier material, in particular with hydroxylapatite, alone is suitable to produce a preparation according to the invention. Preferably, albumin has already previously been removed from the starting material to a high percentage. Separation of the active α1-AT preferably is effected by fractionated elution. Treatment with hydroxylapatite preferably constitutes the terminal purification step.

Surprisingly it has been shown that, although α1-AT is known to be extremely oxidation-labile, the method according to the invention may also be carried out without using β-mercaptoethanol or other oxidation inhibitors which are especially to be avoided when producing pharmaceutical preparations.

The method according to the invention thus preferably is carried out in the absence of β-mercaptoethanol or other oxidation stabilizers, i,e. no buffers containing such a stabilizer are used.

Preferably, the starting material is derived from a plasma pool, in particular such resulting from blood donations of α1-AT normal individuals. For the method of the invention, preferably plasma or a plasma fraction are used, in particular an albumin-depleted starting fraction, preferably a Cohn V-precipitate substantially corresponding to a Cohn IV A fraction (according to Cohn, Review 28 (1941), 395–417). In a further preferred embodiment, it is departed from a pre-purified fraction, it may be departed, e.g., from a commercially obtainable preparation, such as Prolastin.

With the method according to the invention, preferably also a step of inactivating or depleting, respectively, pathogens possibly present is carried out This inactivation/depletion treatment preferably is ensured by a tenside and/or heat treatment, e.g. a heat treatment in the solid state, in particular a vapor treatment according to EP-0 159 311 or EP-0 519 901 or EP-0 674 531, or also with organic solvents and/or detergents, such as, e.g., according to EP-0 131 740 and EP-0 050 061.

Further treatments for inactivation of viruses or pathogens, respectively, also comprise a treatment by means of chemical or chemical/physical methods, e.g. with chaotropic substances according to WO 94/13329 or DE-44 34 538, or a photoinactivation.

Irradiation or nanofiltration are preferred physical methods for depleting viruses within the scope of the present invention.

The method according to the invention preferably is conceptioned such that also the recovery of other proteins is possible, in particular the recovery of transferrin, albumin, orosomucoid and apolipoprotein, which then may be recoveredin a further fraction of the chromatographic treatments according to the invention. The exact conditions for each chromatographic material may easily be found and optimized, respectively, by a skilled artisan who has knowledge of the present invention.

The pH at carrying out the method according to the invention, in particular at elution, preferably ranges between 5.5 and 8.0, in particular around 6.5–6.8. It has also been shown that when carrying out the method according to the invention, the use of a buffer having an ionic strength corresponding to 10 mM of phosphate is suitable.

According to a further aspect, the present invention relates to the use of a carrier material for separating the inactive $\alpha$1-AT from active $\alpha$1-AT. As the solid carrier material for adsorption and separation, preferably an inorganic carrier material, such as hydroxylapatite, is used, or an anion exchanger in the presence of a detergent, in particular Q-Sepharose in the presence of Tween, in a further preferred embodiment.

The present invention will now be explained in more detail by way of the following examples to which, however, it shall not be restricted.

EXAMPLES

Example 1

Purification of $\alpha$1-AT from Cohn V-precipitate (at Present Considered by Applicant to be the Best Mode of Carrying Out the Invention).

Cohn V precipitate is suspended with the three-fold weight of A-buffer (1.2 g/l $Na_2$ $HPO_4$×2 $H_2O$=6.74 mM, 10 g/l NaCl=171 mM, pH 7.0, adjusted with 96% acetic acid) for 4 to 6 h at 4° C. by stirring. Subsequently, $\alpha$1-AT is precipitated over night from this turbid suspension with 17.5% ethanol final concentration at 6° C.

The precipitate centrifuged off is stirred with the 24-fold weight of 10 mM Tris-HCl, pH 10.4 (adjusted with 6 M NaOH) for ½ hour at room temperature and subsequently for 1.5 hours at 40° C., then the pH is adjusted to 6.5 and clarified through a CUNO 50SA filter. 15% v/v of Tween 80 are added to the filtrate and it is stirred for 2 h at 26° C.

The obtained solution is applied to a chromatographic column filled with Q-Sepharose® Fast Flow (Pharmacia) and equilibrated with 25 mM sodium phosphate buffer, pH 6.5, corresponding to 10 mg protein per ml of gel (approximately 2 column volumes), washed with 2.5 column volumes of 25 mM sodium phosphate buffer, pH 6.5 (eluted, largely Tween® 80) and furthermore with 3 column volumes of 60 mM sodium chloride in 25 mM sodium phosphate buffer, pH 6.5 (eluted, Transferrin).

By elution with 3 column volumes of 100 mM sodium chloride in 25 mM sodium phosphate buffer, pH 6.5, the $\alpha$1-AT-containing fraction is obtained with approximately 0.40 to 0.60 plasma units (PU) of $\alpha$1-AT per mg of protein, wherein the activity has been determined by inhibition of elastase according to example 3 (1 PU of $\alpha$1-AT corresponds to approximately 1.3 mg of pure $\alpha$1-AT).

With 3 column volumes of 125 mM sodium chloride in 25 mM sodium phosphate buffer, pH 6.5, then mainly serum albumin and further plasma proteins can be eluted, and with 1 to 2 M of sodium chloride in 25 mM sodium phosphate buffer, pH 6.5, inactive $\alpha$1-AT (practically no elastase inhibition, yet immunoreactive $\alpha$1-AT) and the residual impurities.

With an ultrafiltration membrane (cut-off 30,000 Daltons), the $\alpha$1-AT-containing fraction is concentrated approximately 30-fold and diafiltered with 0.15 g/l $Na_3$ citrate×2 $H_2O$=0.5 mM.

Subsequently, the diafiltrate obtained is lyophilized. The lyophilized powder is moistened to a residual water content of 7.5+/−0.5% and subjected to the S-TIM 4-treatment according to EP-0 159 311 (10 h at 60° C. and 1 h at 80° C.)

The treated powder is dissolved in 10 mM sodium phosphate buffer, pH 6.8, to approximately 10 mg/ml protein and applied to a chromatographic column filled with ceramic hydroxyapatite (Macropep type I, grain size 80 $\mu$m, Bio-Rad) and equilibrated with 10 mM sodium phosphate buffer, pH 6.8, corresponding to 10 mg of protein per ml column bed (approximately 1 column volume).

By elution with 5 column volumes of 40 mM sodium phosphate buffer, pH 6.8, the $\alpha$1-AT-containing fraction is obtained with approximately 0.90 to 1.05 plasma units (PU) of $\alpha$1-AT per mg of protein.

With 3 column volumes of 100 mM sodium phosphate buffer, pH 6.8, it is then possible to elute mainly inactive $\alpha$1-AT, serum albumin and further plasma proteins, and with 500 mM sodium phosphate buffer, pH 6.8, the residual impurities.

It has been shown that with this purification method, $\alpha$1-AT with a high specific activity of 1.0 PU/mg (corresponds to 130% relative plasma $\alpha$1-AT activity) can be obtained. The result is illustrated in the following Table 1.

TABLE 1

|  | Spec. Activity PU/mg | Purific. | Total Yield/ % Plasma |
|---|---|---|---|
| Plasma | 0.014 | 1.0 | 100 |
| After Hydroxyapatite | 1.0 | 70.0 | 14 |

The $\alpha$1-AT product Prolastin (Cutter) present in the pharmaceutical market has a purity of between 45–80% according to the producer's information and yields a specific activity of 0.60 PU/mg in the elastase inhibition assay (corresponds to 78% relative plasma $\alpha$1-AT activity).

Example 2

Purification of $\alpha$1-AT (Serva) by Means of Ceramic Hydroxyapatite $\alpha$1-AT from Serva which, with at least 95% purity (according to the producer's information determined by means of SDS gel) had the highest specific activity $\alpha$1-AT of 0.81 PU/mg measured so far, was also further treated via ceramic hydroxyapatite. The combined fractions yielded a specific activity of 0.92 PU/mg (corresponds to approximately 120% relative plasma $\alpha$1-AT-activity). In the reducing SDS excel-gel, an unambiguous separation of inactive $\alpha$1-AT and other contaminating proteins is visible by means of silver staining of the proteins.

Example 3

Instruction for Measurement of Elastase Inhibition

The assay was made following the instructions by J. Bieth, B. Spiess and C. G. Wermuth (1974). The synthesis and analytical use of a highly sensitive and convenient substrate of elastase, Biochem. Med. 11(4), 350–357, and J. Travis and D. Johnson (1981), Human alpha-1-Proteinase Inhibitor, Methods of Enzymology 80, 754–765, respectively.

Inhibition is calculated according to: %=(1-(dA/min)$_{sample}$/(dA/min)$_{blank\ value}$) *100. The inhibition of the samples should lie in a range of from 20 to 50% inhibition and subsequently is converted into plasma units by means of the standard line.

Example 4

Characterization of Various α1-AT Products by Means of Elastase Inhibition

TABLE 2

| Product | Protein/ mg/ml | Activity/ Pu/ml | Spec. Act./ PU/ mg | Purity | Purification | Relative Plasma-A1AT-Actitvity | Main Bands of A1AT in IEF-Gel | | | |
|---|---|---|---|---|---|---|---|---|---|---|
| | | | | | | | pI = 4.55–4.58 | pI = 4.47–4.51 | pI = 4.41–4.45 | pI = 4.35–4.39 |
| Plasma | 70.00 | 1.00 | 0.014 | 1.7% | 1.0 | 100.0% | + | + | + | +/− |
| after hydroxyl-apatite | 1.21 | 1.22 | 1.009 | 117.8% | 70.6 | 131.1% | + | + | + | + |
| Serva (# 13694) | 0.44 | 0.36 | 0.814 | 95.0% | 57.0 | 105.8% | + | + | + | − |
| Sigma (# A-9024) | 0.49 | 0.15 | 0.299 | 34.9% | 20.9 | n.c. | + | + | + | − |
| Prolastin (Cutter) | 41.99 | 23.95 | 0.570 | 66.6% | 39.9 | n.c. | + | + | + | − |

+/− hardly visible
+ present
− not present
n.c. not calculated

| | |
|---|---|
| Tris: | 0.2 M Tris-HCl, pH 8.0 |
| Tris+: | Tris with 0.1% human serum albumin (HSA) admixed shortly before use. |
| Elastase: | 6% elastase (from porcine pancreas, Boehringer Mannheim) is diluted 1:1000, sterile-filtered and frozen at −20° C. |
| Substrate: | 22.5 mg succinyl (alanine)$_3$-para-nitroanilide (Bachem Feinchemikalien AG, Switzerland) is dissolved in 5 ml of dimethyl formamide and stored at 4° C. |

The samples are diluted with Tris+ up to the respective concentration.

25 μl of elastase are diluted with 275 μl of Tris+ (warmed to 25° C. in a water bath) and incubated with 100 μl of sample for 3 min at 25° C. Then the substrate is diluted 1:10 with Tris+, 200 μl thereof are added to the formulation and the extinction increase at 405 nm and 25° C. is immediately measured for 5 minutes. As the blank value of inhibition, 100 μl of Tris+ are added to the formulation instead of a sample.

In the above formulation, the blank value yields between 0.05 to 0.06 dA/min. As standard curve, a dilution series 1:100 to 1:400 of reference plasma (Inmmuno AG 1A3E) is used. From a 1:50 predilution (frozen in aliquots at −20° C.), the Prolastin (Cutter) is diluted 1:80 (1:4000 dilution) with Tris+ and co-measured at each measurement series with the 1:150 dilution of the reference plasma. When the deviation is too high as compared to the standard line, this measurement series should be discarded, or the results should only be viewed as approximate values.

What is claimed is:

1. A method of preparing a purified biologically active alpha 1-antitrypsin (α1-AT) preparation containing an α1-AT isomer having a pI of between 4.3 and 4.4 comprising: providing a starting material containing active and inactive α1-AT, wherein the starting material is a plasma fraction obtained from pooled human plasma; providing a hydroxyapatite substrate; passing said starting material containing α1-AT over said hydroxyapatite substrate; eluting a biologically active α1-AT biologically active α1-AT preparation having a pI of between 4.3 and 4.4; and passing said biologically active α1-AT preparation over an anion exchange material in the presence of a detergent.

2. The method according to claim 1, wherein said eluting step is on said hydroxyapatite is conducted with a buffer having a pH of between 5.5 and 8.0.

3. The method according to claim 2, wherein said eluting step on hydroxyapatite is conducted with a buffer having a pH of between 6.5 and 6.8.

4. The method according to claim 1, wherein said starting material is an albumin-depleted plasma fraction.

5. The method according to claim 1, wherein said starting material is Cohn V precipitate.

6. The method according to claim 4, wherein said starting material is a pre-purified α1-AT preparation fraction.

7. The method according to claim 1, wherein said hydroxyapatite is a ceramic hydroxyapatite.

8. The method according to claim 1, wherein said eluting step on said hydroxyapatite is conducted with a buffer which comprises a salt having an ionic strength corresponding to 60 mM of phosphate.

9. The method according to claim 1, wherein said eluting step on said hydroxyapatite is conducted with a buffer which comprises a salt having an ionic strength corresponding to 40 mM of phosphate.

10. The method according to claim 1, wherein said eluting step on said hydroxyapatite is conducted with a buffer which comprises a salt having an ionic strength corresponding to 50 to 130 mM of phosphate.

11. The method as set forth in claim 1, further comprising a pathogen inactivation step.

12. The method as set forth in claim 11, wherein said pathogen inactivation step includes at least one of a solvent, a detergent or a heat treatment step.

13. A method for purifying biologically active α1-AT including α1-AT isomers having pIs of between 4.3 and 4.4 from an alpha 1-AT-containing fraction which is obtainable from a human plasma pool comprising: Adjusting the pH of said α1-AT-containing fraction to about 6.5, absorbing said acidified α1-AT-containing fraction onto a chromatographic anion exchanger in the presence of a detergent, and eluting said biologically active α1-AT from said chromatographic anion exchanger including α1-AT isomers having pIs of between 4.3 and 4.4.

14. A method according to claim 13 in which said elution is carried out at a pH ranging between 5.5 and 8.0.

15. A method according to claim 13 in which said elution is carried out at a pH ranging between 6.5 and 6.8.

* * * * *